(12) United States Patent
Hiraoka et al.

(10) Patent No.: US 8,496,626 B2
(45) Date of Patent: Jul. 30, 2013

(54) SAFETY NEEDLE ASSEMBLY

(75) Inventors: Yuki Hiraoka, Osaka (JP); Ken Suzuki, Osaka (JP)

(73) Assignee: Nipro Corporation, Osaka (JP)

( * ) Notice: Subject to any disclaimer, the term of this patent is extended or adjusted under 35 U.S.C. 154(b) by 157 days.

(21) Appl. No.: 12/225,830

(22) PCT Filed: Apr. 27, 2007

(86) PCT No.: PCT/JP2007/059259
§ 371 (c)(1),
(2), (4) Date: Sep. 30, 2008

(87) PCT Pub. No.: WO2007/126085
PCT Pub. Date: Nov. 8, 2007

(65) Prior Publication Data
US 2009/0163875 A1    Jun. 25, 2009

(30) Foreign Application Priority Data
Apr. 28, 2006   (JP) ................................. 2006-126889

(51) Int. Cl.
*A61M 5/32* (2006.01)
(52) U.S. Cl.
USPC .......................................... 604/192; 604/198
(58) Field of Classification Search
USPC .............................. 604/192–198, 110, 164.08
See application file for complete search history.

(56) References Cited

U.S. PATENT DOCUMENTS 6,969,372 B1    11/2005  Halseth
7,438,703 B2 *  10/2008  Barrus et al. ................. 604/192
7,497,845 B2 *   3/2009  Reid ......................... 604/164.08

2002/0072716 A1   6/2002  Barrus et al.
2003/0049553 A1   3/2003  Nakamura
2005/0049553 A1   3/2005  Triplett et al.

FOREIGN PATENT DOCUMENTS

| JP | 2004-510555 | 8/2004 |
| WO | WO 02/30496 | 4/2002 |
| WO | WO 03/028784 | 4/2003 |
| WO | WO 2005/049109 | 6/2005 |

OTHER PUBLICATIONS

Notice of Reasons for Rejection issued to Mexican Application No. MX/a/2008/-013742, mailed Jul. 22, 2011.

* cited by examiner

*Primary Examiner* — Kevin C Sirmons
*Assistant Examiner* — Imani Hayman
(74) *Attorney, Agent, or Firm* — Dilworth & Barrese, LLP

(57) ABSTRACT

Provided is a safety needle assembly for protecting a needle point, a safety type needle assembly having a curved portion, to which an erroneous piercing preventing mechanism is added, or a safety type Hoover needle assembly thereby to prevent the piercing accident. The safety needle assembly includes a needle having a point at its leading end, a hub for holding the root end portion of the needle, and a leading end protecting portion. The safety needle assembly further includes a restricting portion for restricting the distance between the needle and the hub, in that the leading end protecting portion includes a mechanism for warping the needle point, when the leading end protecting portion moves the leading end of the needle to a projecting position, thereby to accommodate the needle point in the inner side of the leading end protecting portion, so that the leading end of the needle is protected.

14 Claims, 16 Drawing Sheets

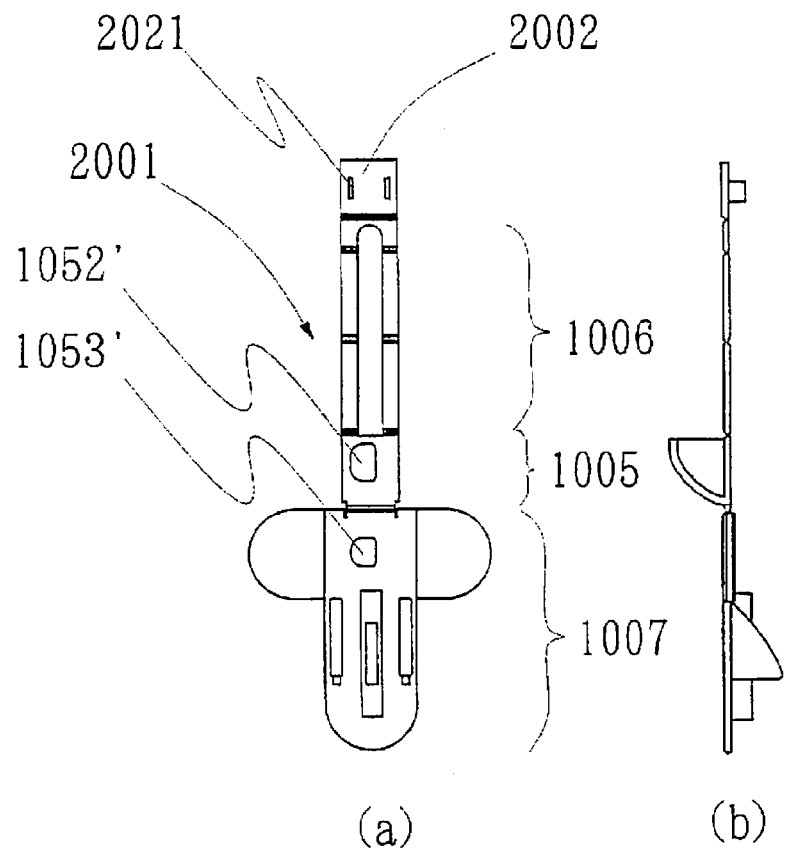
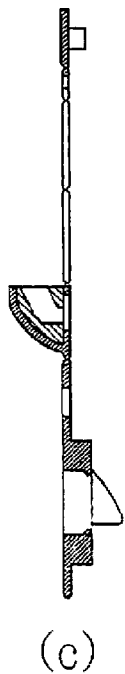
Fig. 15

SAFETY NEEDLE ASSEMBLY

TECHNICAL FIELD

The present invention relates to a safety needle assembly for guarding a needle tip, and particularly to a safety needle assembly in which a needle having a bend portion is employed, and more particularly to a Huber needle assembly serving as an insertion needle for use in a subcutaneous implant-type catheter access port. The present invention relates even more particularly to a Huber needle assembly including a safety mechanism for preventing accidental needlestick designed in such a way as to ensure the distal end of the needle of a Huber needle assembly inserted in a catheter access port is covered when it is withdrawn therefrom.

BACKGROUND ART

A surgical needle normally employed as the needle for, for example, insertion in a subcutaneous implant-type catheter access port is not a common injection needle, but rather a Huber needle of a shape in which the cutting surface is perpendicular to the direction of insertion in such a way as to prevent coring when the septum of the port is punctured. Huber needles that have a bend portion of 90° and to which wings parallel in the horizontal direction are fixed thereto are employed for uses including continuous infusion.

DISCLOSURE OF THE INVENTION

Problems to be Solved by the Invention

Inadvertent needle stick of the medical staff or the patient following use is a problem commonly associated with needle assemblies including Huber needle assemblies that have wings provided in parallel in the horizontal direction such as this. In addition, it is recognized that merely scratching the skin with an unprotected sharp tip of a used needle may be sufficient to cause transmission of an infectious disease. In the USA, where the "Needlestick Safety and Prevention Act" has been enacted, the use of a safety-type needle assembly and more particularly a safety Huber needle assembly is needed.

As an example of a safety-type needle assembly having a bend portion for resolving the problem described above, a folding wing-type needle assembly including an approximately 90° bend portion and in which flat wings are able to be moved to a guarded position, where contact with the distal end of the needle is prevented, has been disclosed (see Patent Document 1).
Patent Document 1: Published Japanese Patent Application No. 2004-510555

In the aforementioned safety-type needle assembly, contact of the needle with the fingertips is rendered unlikely as a result of the wings being simply folded down around the needle and, as a result, inadvertent needle stick can be prevented. Accordingly, inadvertent needle stick can be prevented by a simple operation using the aforementioned needle assembly.

However, in the aforementioned needle assembly, in order for the wings to guard the needle tip simultaneously with the needle being withdrawn from the living body, the wings must be of a sufficient weight to ensure falling under their own weight and, accordingly, when the needle assembly is deployed, the wings press against the patient and cause increased patient discomfort. Moreover, when the aforementioned needle assembly is deployed in the arm or chest regions of a patient, expansion of the wings to lie perpendicular to the direction of gravity is prevented, which in turn renders it difficult for the wings to guard the needle tip simultaneously with the needle being withdrawn from the living body. In addition, since the return of the wings in the aforementioned needle assembly is prevented by the provision of a shallow stepped stopper portion and, accordingly, contact between the needle and the body is prevented so long as only a light force is applied thereto, prevention of needle exposure becomes difficult with a strong external force on the wings.

Furthermore, the aforementioned needle assembly does not constitute a structure in which the area of the distal end of the needle in the section thereof that comes into contact with the living body is covered. For this reason, there is potential for the bodily fluids adhered to the needle to splash or come into contact with the body and, in turn, there is potential for infectious diseases such as HIV or hepatitis to be transmitted by the contact or splash of these bodily fluids.

It is an object of the present invention to prevent needlestick injuries by providing a safety needle assembly for guarding a needle tip, by further providing a safety-type needle assembly having a bend portion and to which an inadvertent needlestick prevention mechanism is fitted, and more particularly by providing a safety-type Huber needle assembly.

Means for Solving the Problems

That is, the present invention constitutes a needle assembly including a needle in which a cutting blade is formed in a distal end; a hub for holding a proximal end portion of the needle; and a distal end guarding portion,
wherein the needle assembly includes a restraining portion for restricting a distance between the needle and the hub,
the distal end guarding portion includes a mechanism for flexing the needle tip,
and the distal end of the needle is guarded by, when the distal end guarding portion is moved to a position to guard the distal end of the needle, the needle tip being flexed by the aforementioned mechanism to house the needle tip in the interior of the distal end guarding portion. In addition, the present invention also constitutes a needle assembly in which, as the aforementioned needle, a Huber needle is employed. Furthermore, the present invention constitutes a needle tip guarding mechanism including: a needle in which a cutting blade is formed in a distal end; a hub for holding a proximal end portion of the needle; and a distal end guarding portion, in which the needle tip guarding mechanism includes a restraining portion for restricting a distance between the needle and the hub, the distal end guarding portion includes a mechanism for flexing the needle tip, and the distal end of the needle is guarded by, when the distal end guarding portion is moved to a position to guard the distal end of the needle, flexure of the needle tip by the aforementioned mechanism to house the needle tip in an interior of the distal end guarding portion

Effects of the Invention

The present invention of the needle assembly as described above can be effectively used as a safety needle assembly irrespective of whether the needle has a bend portion or not and, more particularly, it can be effectively used as a subcutaneous implant-type catheter access port insertion needle that has a bend portion and, furthermore, it is ideal for employment in medical treatment methods that involve the use of a catheter. In addition, as the cutting blade is not caused to re-protrude when an external force is applied to the needle tip in the guarded state, the safety needle assembly of the present invention offers a high degree of safety and, as it can be employed in such a way that the cutting blade is guarded simultaneously with the needle being removed from a living body, the present invention offers an improved degree of safety. In addition, as the needle assembly of the present invention describes a structure in which blood and bodily fluids adhering to the needle tip can be prevented from coming into contact with the body, it constitutes an ideal needle assembly for preventing secondary medical injuries.

BRIEF DESCRIPTION OF THE DRAWINGS

FIG. 15 A is a front view of the connection body of the needle assembly of FIG. 9, B is a left-side view of the connection body of A, and C is a vertical cross-sectional view of the connection body of A;

PREFERRED MODE FOR CARRYING OUT THE INVENTION

The needle assembly of the present invention shall be hereinafter described in detail with reference to the figures.

Figure 1:
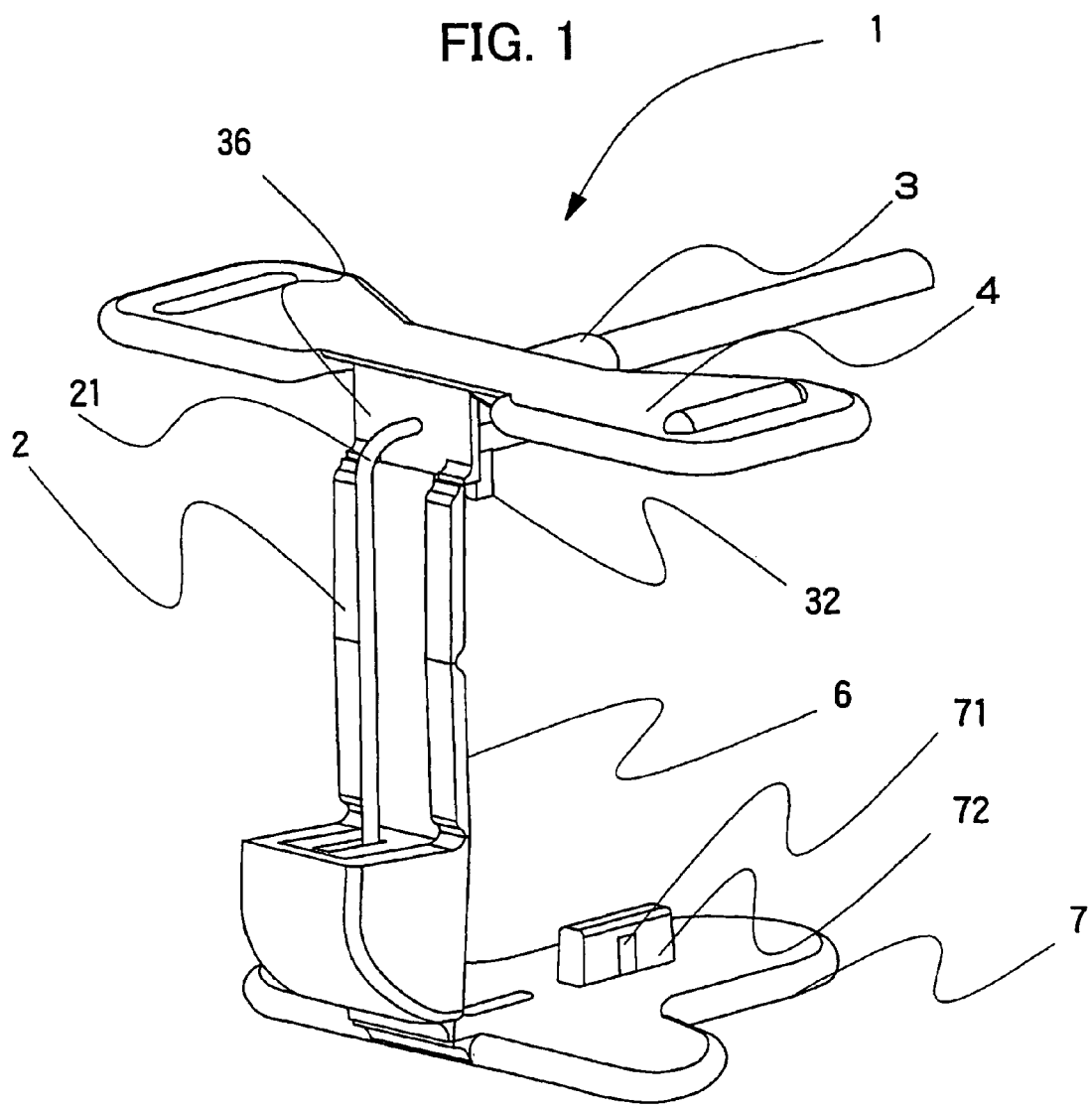
FIG. 1 is a perspective view of the post-use state of a first embodiment of the needle assembly of the present invention.
Figure 2:
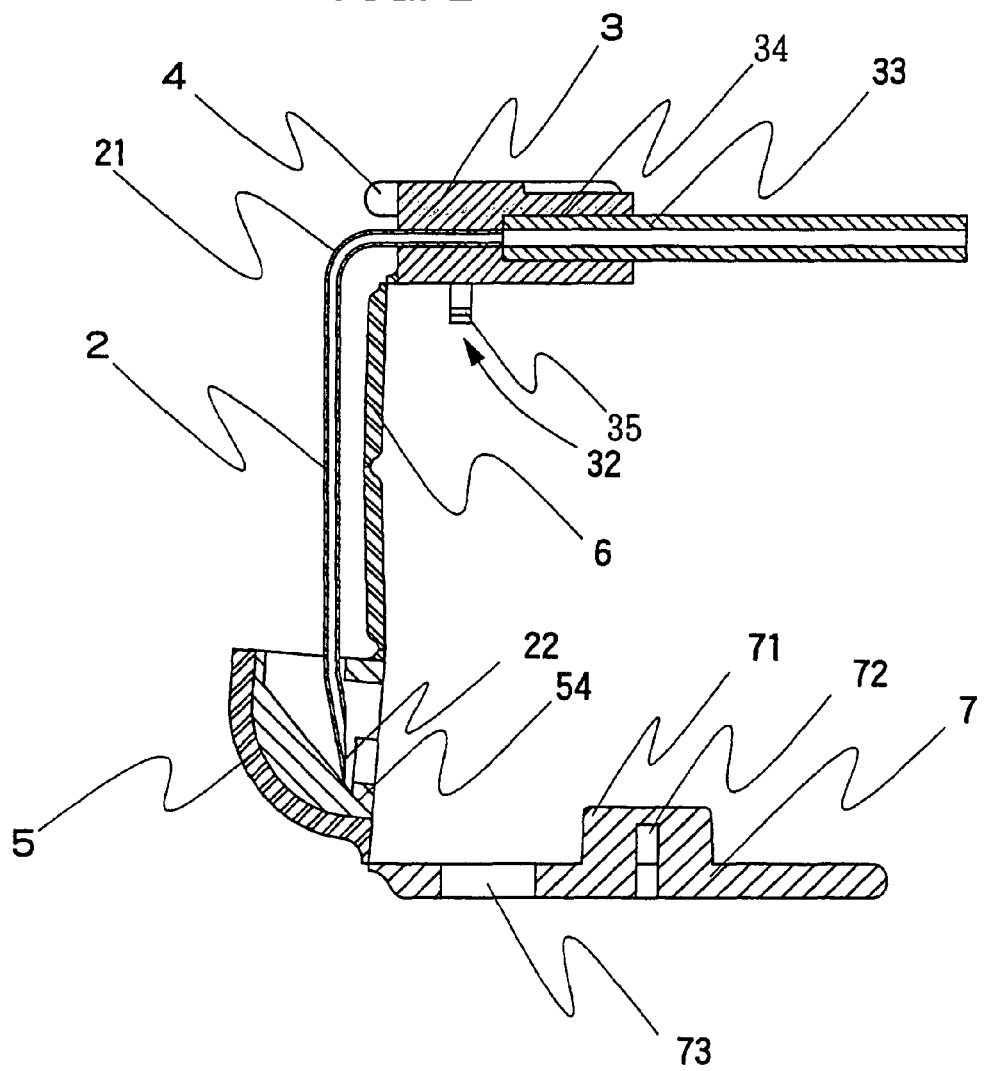
FIG. 2 is a vertical cross-sectional view of the post-use state of a first embodiment of the needle assembly of the present invention.

FIG. 1 is a perspective view of the post-use state of the needle assembly when the needle distal end is housed. FIG. 2 is a cross-sectional view of the needle assembly of the present invention in the state of FIG. 1. A needle assembly 1 includes a needle 2 having a bend portion 21 of an approximately 90° bend, and a hub 3 for holding the proximal end portion of the needle 2.

The needle assembly 1 includes a distal end guarding portion 5 for guarding the distal end of the needle 2, a restraining portion 6 provided between the distal end guarding portion 5 and the hub 3, and a fixing portion 7 that fixes to the skin or the like of a living body. The aforementioned fixing portion 7 links with the distal end guarding portion 5. The aforementioned needle is mounted in the hub provided essentially horizontal to the plane of deployment of the living body, and the needle tip bends downward. While a Huber needle of a shape in which the cutting face is perpendicular to the direction of insertion of the needle is employed as the needle 2 of the embodiment of FIG. 1, other surgical needles may also be employed. While the aforementioned bend of the bend portion in FIG. 1 is approximately 90°, there are no particular restrictions to the bend being approximately 90°. However, as the needle is able to be inserted in the living body by an operation involving merely a grip portion being held between the fingers and pressed from above and, moreover, the needle tube is provided to extend in a direction horizontal to the deployment plane, whereby the arrangement of the tube is also simple, the bend of the bend portion is preferably approximately 90°.

As shown in FIG. 2, following usage, a needle distal end portion 22 of the needle 2 of the embodiment of FIG. 1 is housed in the interior of the distal end guarding portion 5. The distal end guarding portion 5 is designed so that, when the needle distal end portion 22 is housed in the interior of the distal end guarding portion 5 as shown in FIG. 2, the distance thereof to the hub 3 is restricted by the restraining portion 6 so that, accordingly, movement toward the distal end from the state in which the needle tip is housed as shown in FIG. 2 is prevented. In addition, the distal end guarding portion 5 describes a needle tip surrounding structure and encloses the needle distal end portion 22 of the needle 2 with play and, because the positional relationship between the distal end guarding portion 5 and the needle distal end portion 22 is restricted by the restraining portion 6, projection of the needle beyond the needle tip surrounding structure to the exterior of the distal end guarding portion 5 can be prevented. Furthermore, when a state in which the needle distal end portion 22 is enclosed within the interior of the distal end guarding portion with play is established, the exterior of the distal end guarding portion 5 and the needle distal end portion are in contact as described later, and the needle distal end portion 22 is housed in the interior of the distal end guarding portion 5 due to the flexibility of the needle and/or the needle-contacting section of the distal end guarding portion. Moreover, a tube 33 connects to a tube-connecting hole 34 of the hub 3 to impart communication between the cavity of the needle 2 and the tube cavity.

Figure 3:
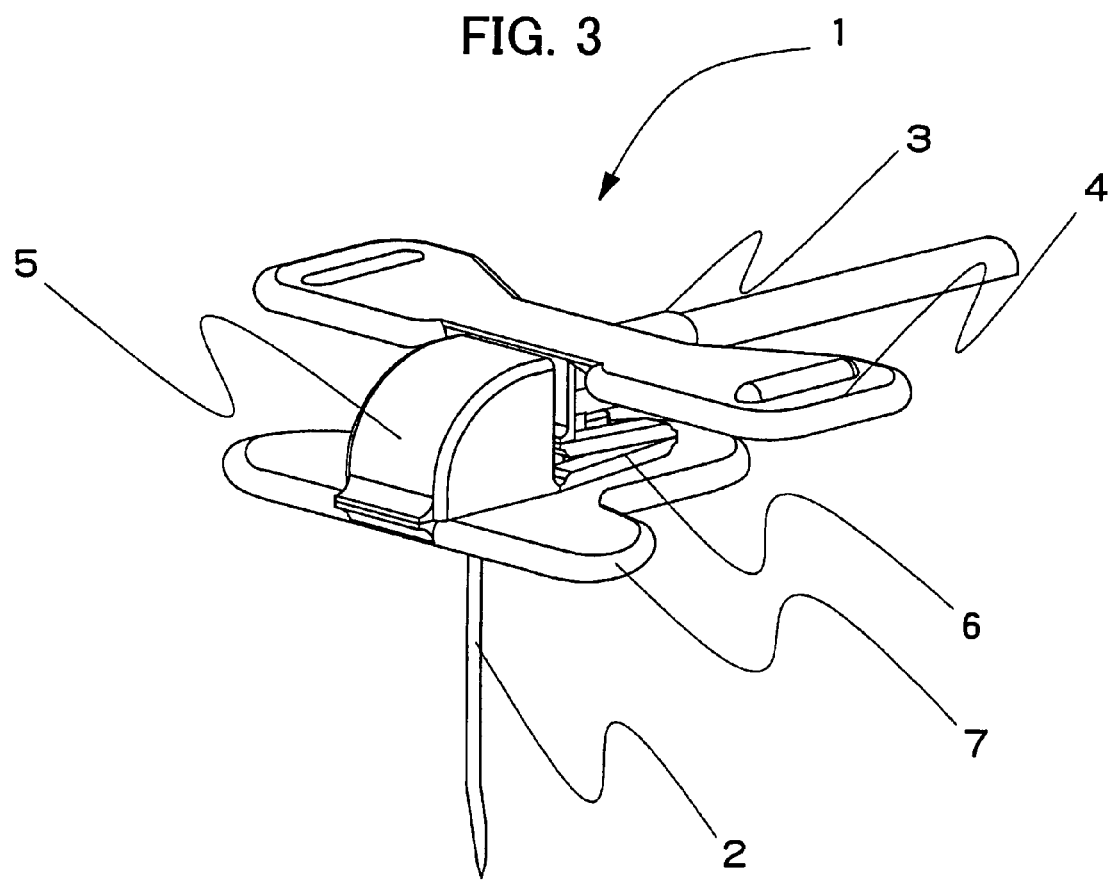
FIG. 3 is a perspective view of the pre-use state of the needle assembly of FIG. 1.
Figure 4:
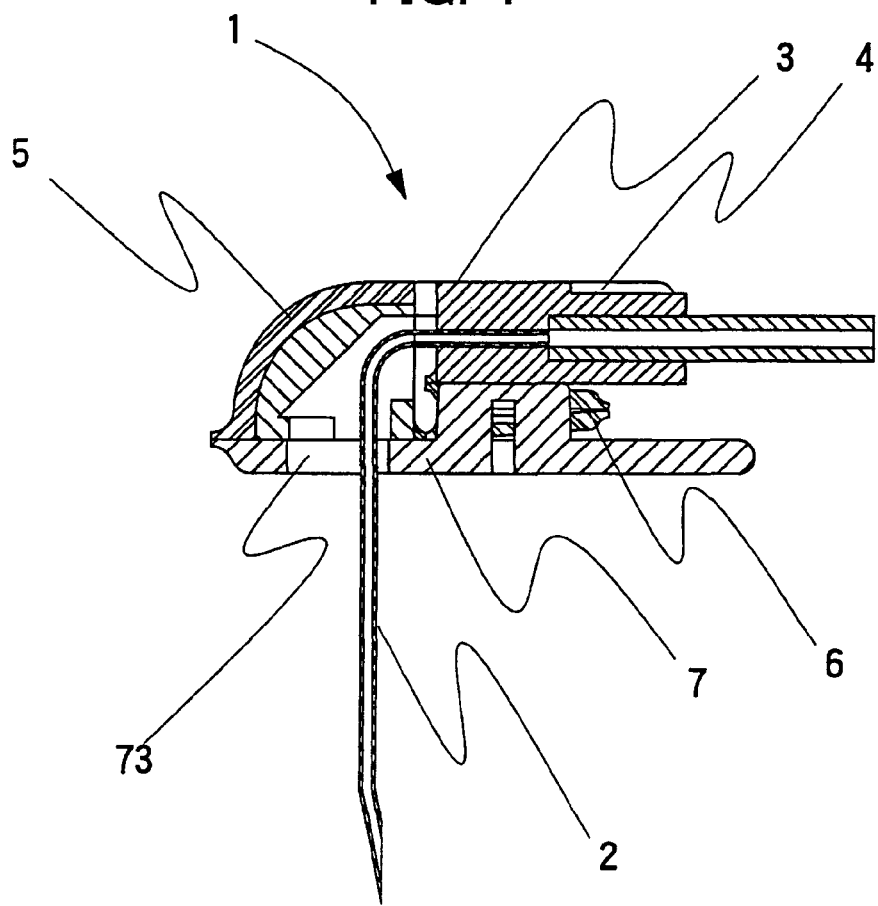
FIG. 4 is a cross-sectional view of the pre-use state of the needle assembly of FIG. 1.

The pre-use state to the post-use state in which the needle distal end portion 22 of the needle 2 is guarded of the embodiment of FIG. 1 is shown in the diagrams. FIG. 3 is a perspective view of the pre-use state of the needle assembly 1 of the present invention, and FIG. 4 is a vertical cross-sectional view of the needle assembly 1 of the present invention of the state of FIG. 3. In the pre-use state of the needle assembly 1, the restraining portion 6 is folded as shown in FIG. 3, and the hub 3 and the fixing portion 7 are provided in a state in which an engaging portion 32 of the hub 3 and a connecting portion 71 of the fixing portion 7 are connected. As shown in FIG. 1, an engagement-receiving portion 72 configured as an opening is provided in the connecting portion 71 and, as a result of the engagement thereof with an engaging protrusion 35 of the engaging portion 32, the hub 3 and the fixing portion 7 are connected. The needle 2 is provided in a state in which it passes through a first aperture portion 51 of the distal end guarding portion 5 to pass along the distal end guarding portion 5 and, passing out of a second aperture portion 52, it passes further along a needle passage 73 of the fixing portion 7 to project from the fixing portion 7. While in the pre-use state of the needle assembly, wing portions 4 may be held to insert the needle into living body, instead of wing portions, a grip portion may be provided, and this grip portion held as the needle is inserted into the living body.

Figure 5:
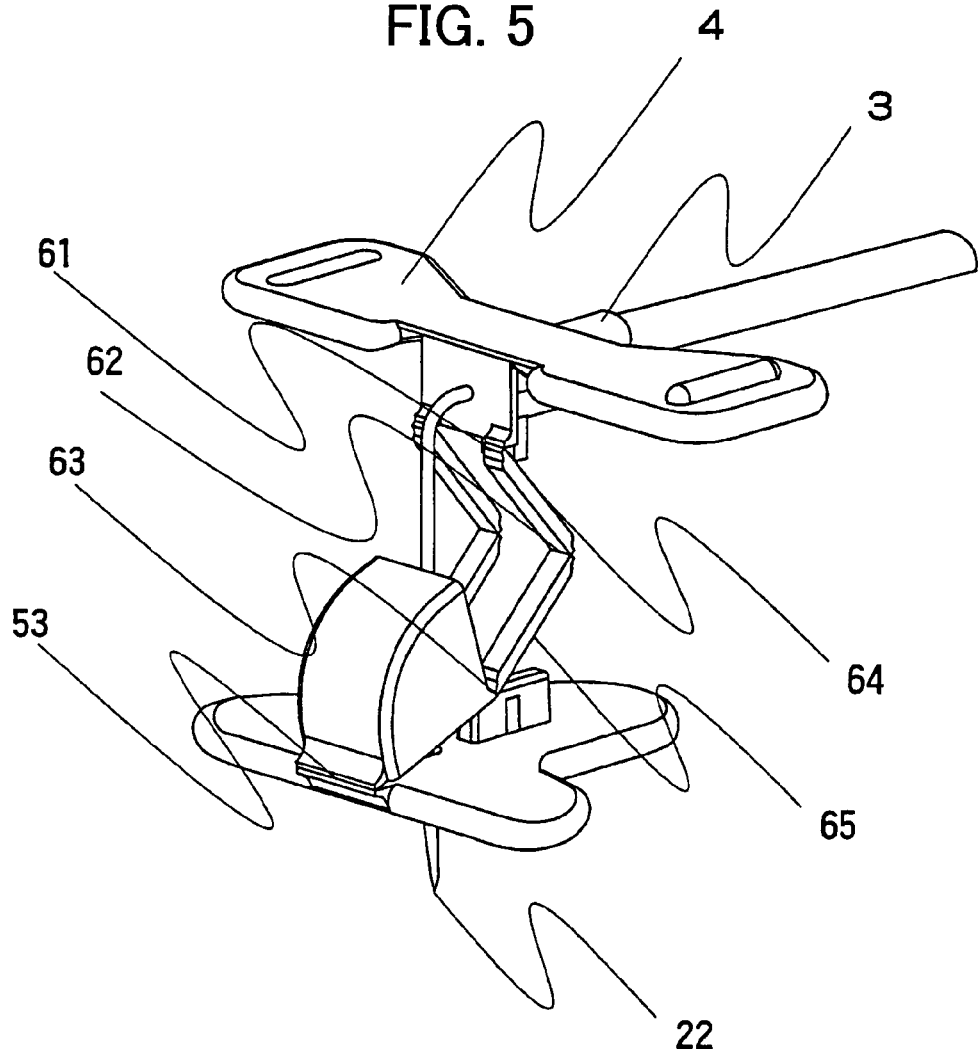
FIG. 5 is a perspective view showing the transition from the pre-use state of the needle assembly of FIG. 1 to the state of FIG. 1.
Figure 6:
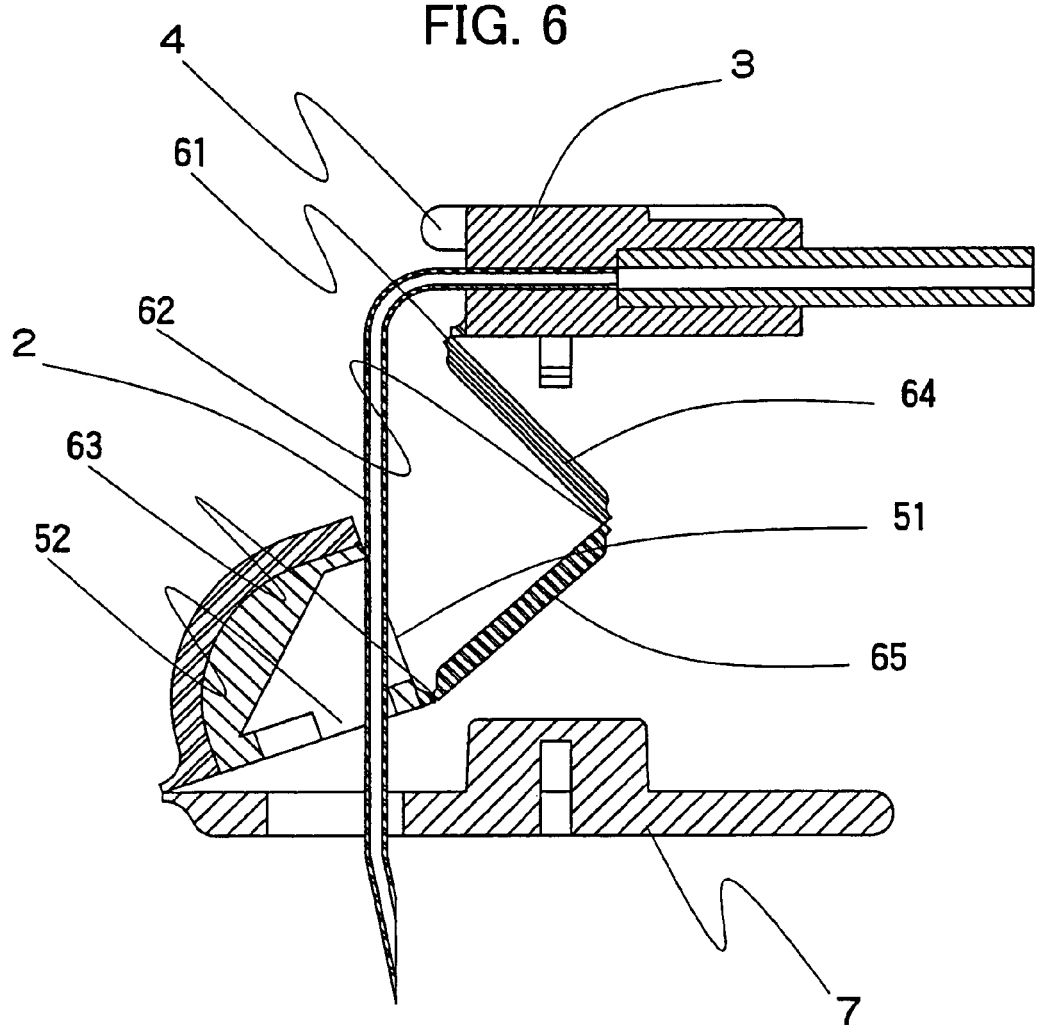
FIG. 6 is a cross-sectional view showing the transition from the pre-use state of the needle assembly of FIG. 1 to the state of FIG. 1.

In the post-use state of the embodiment of the needle assembly of the present invention of FIG. 1, the needle assembly 1 lies in an intermediate state as shown in FIG. 5 and FIG. 6 in which the hub 3 and the fixing portion 7 are separated. In a state in which the needle 2 has penetrated the first aperture portion 51 located in the needle proximal end-side and the second aperture portion 52 located in the needle distal end-side and furthermore, in which it has penetrated the needle portion 73, the distal end guarding portion 5 and the fixing portion 7 are moved relatively in the needle distal end direction. Hinge portions 61 to 63 are provided in the restraining portion 6 of the needle assembly 1 as shown in FIG. 5 and FIG. 6 and, in addition, a hinge portion 53 is provided between the distal end guarding portion 5 and the fixing portion 7. Provided the restraining portion can be converted from the folded state shown in FIG. 3 to the extended state shown in FIG. 1, there are no particular restrictions to the provision of the hinge portions or to the number thereof, and a restraining portion having a slidable extending member, or hinge portions of a wedge-shaped structure or hinge portions rotationally movable about a hinge including a rotary pin may be employed, or bendable members including linear members such as a strap member may also be employed. The hinge portions of the restraining portion 6 shown in FIG. 6 allow it to be compactly, foldably-housed and, moreover, because the restraining portion can be formed from a material that does not elongate in the length direction, the restraining portion can satisfactorily demonstrate the function of restricting the distance between the distal end guarding portion and the hub with little change in the length direction. In addition, as shown in FIG. 5, the needle assembly 1 includes two restraining portions 6 between a hub front face 36 and the distal end guarding portion 5. While there are no particular restrictions to the number of restraining portions 6, where a structure for stably connecting the hub and the fixing portion including two engaging portions 32 interposed at both sides of the connecting portion 71 is to be adopted, as they can be arranged in a space-saving state in both sides of the connecting portion 71, it is preferable for two restraining portions 6 to be provided.

Figure 7:
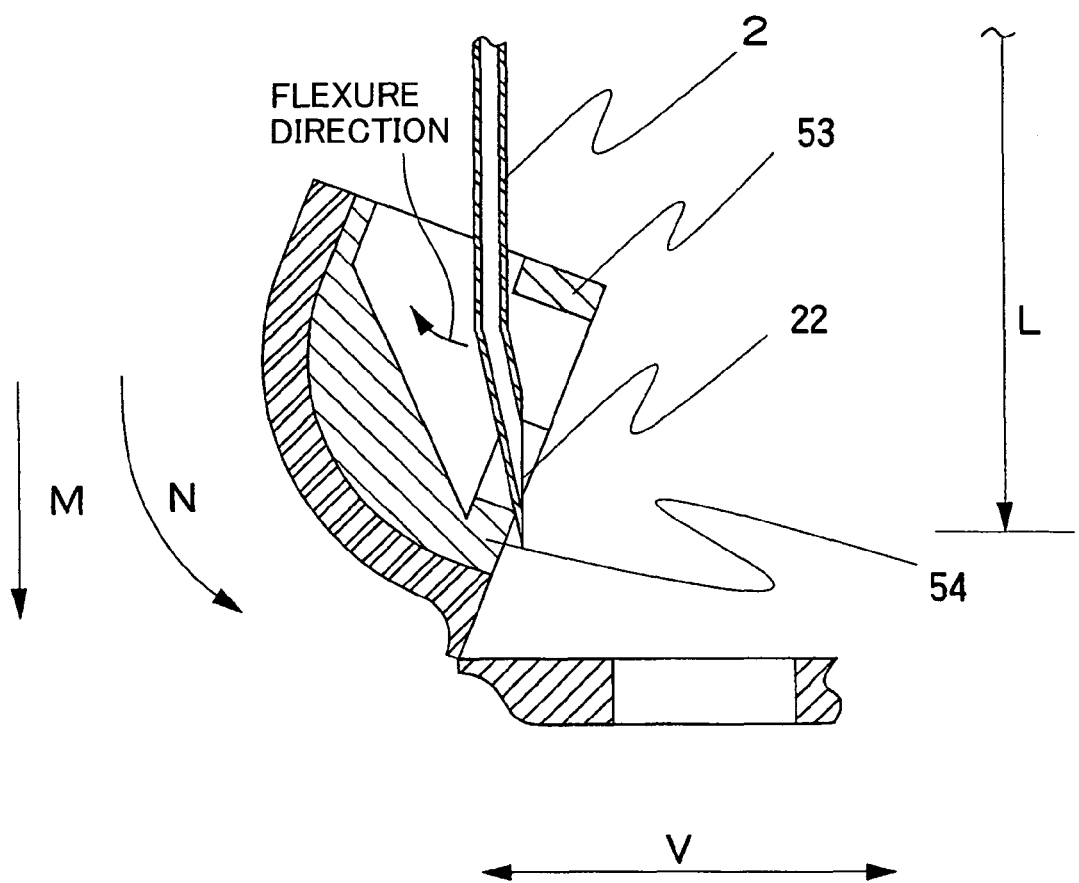
FIG. 7 is a cross-sectional view of the state of the needle assembly of FIG. 1 when the distal end guarding portion guards the needle distal end.

The distal end guarding portion 5 and fixing portion 7 are relatively moved in the needle tip direction from the state shown in FIG. 6 of the needle assembly 1 of the present invention, the fixing portion 7 moves beyond the needle distal end to separate from the needle, and the needle tip is housed in the interior of the distal end guarding portion. The needle 2 is housed in the distal end guarding portion 5 at this time due to the elasticity of the needle as shown in FIG. 7. The mechanism described below for housing a needle tip in a distal end guarding portion has been considered. As the positional relationship between the distal end guarding portion 5 and the needle tip 22 is being restricted by the restraining portion 6 (not shown in FIG. 7), a state in which the needle 2 is in contact with the interior of a fulcrum portion of the distal end guarding portion 5 and the exterior of a needle tip retraction preventing portion 54 is established. Furthermore, when the distal end guarding portion 5 is caused to move relatively from the state of FIG. 7 due to the application of a force M in the distal end direction of the needle 2, the needle tip 22 is subject to a force N in the relative rotational direction about the fulcrum portion 53. Due to the elasticity thereof, the portion of the needle 2 in proximity of the needle tip is flexed to the interior of the distal end guarding portion 5. As a result of this flexure, a length component L of the needle 2 contracts in the distal end direction, the distal end guarding portion moves relatively beyond the needle tip 22 to the distal end-side, and the needle tip 22 is housed in the interior of the distal end guarding portion 5. The needle tip retraction preventing portion 54 extends in the length direction of the needle and, as a result, it holds the needle tip 22 in the interior of the distal end guarding portion 5 and, because the distal end guarding portion 5 does not include a structure in its interior for flexing the needle, the needle tip 22 does not protrude to the exterior.

In the needle assembly 1 of the present invention, an end portion of the restraining portion 6 links with the distal end guarding portion 5 and, while there are no particular restrictions to this linking section, the section where the restraining portion 6 links with the distal end guarding portion 5 in a vertical direction V to the length direction of the needle 2 is preferably one of the same position as the fulcrum portion or the fulcrum guarding position on the opposing side of the needle with respect to the fulcrum portion. Furthermore, when the needle tip is to be guarded by the aforementioned distal end guarding portion, while the distal end guarding portion can be held by the hand and caused to move in the needle distal end direction, when a fixing portion connected to the distal end guarding portion is provided, the needle distal end can be easily guarded, while pressing the fixing portion in the ground plane direction, by lifting the needle hub upward.

Figure 8:
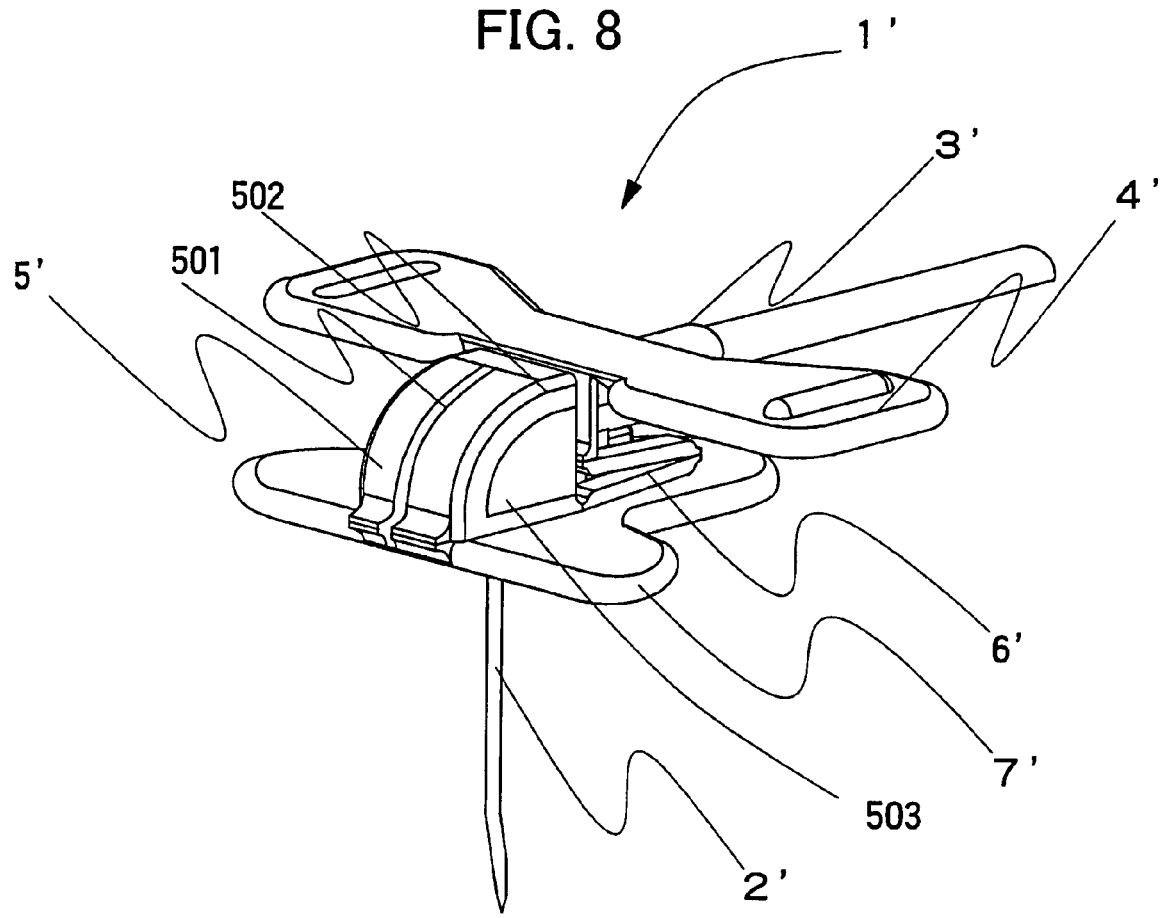
FIG. 8 is a perspective view of the pre-use state of a second embodiment of the needle assembly of the present invention.

The distal end guarding portion 5' of a needle assembly 1' of the present invention may constitute a structure in which the fulcrum portion 53 and the needle tip retraction preventing member 54 constitute the same member, and may constitute a structure in which the interior member including the fulcrum portion 53 and the needle tip retraction preventing member 54 are inlaid into the interior of an exterior member from which the exterior of the distal end guarding portion 5' is constituted. In addition, as shown in FIG. 8, a structure in which an interior member 503 including a fulcrum portion 53 and a needle tip retraction preventing member 54 is provided in the interior of an exterior member 502 including a slit 501 from which the exterior of the distal end guarding portion 5' is constituted may also be adopted. If a structure such as this is adopted, subsequent to a needle shaft being arranged through the slit into the interior of the distal end guarding portion 5 as shown in the state of, for example, FIG. 1, an interior member 504 can be inserted from the lateral direction into an exterior member 503 to establish a state in which the distal end of the needle 2' can be guarded by the distal end guarding portion 5'. By the adoption of a structure such as this in which a slit is provided in the distal end guarding portion and in which, with the distal end guarding portion constituted from two members, an interior member including the fulcrum portion 53 and needle tip retraction preventing portion 54 is inlaid into an exterior member in a state in which the shaft of the needle is arranged in a position to penetrate the distal end tip guarding portion material, there is no need in the needle assembly of the present invention for the distal end guarding portion material to be penetrated once the needle and hub have been joined and, accordingly, the operation for joining the needle and the hub is simplified, and the manufacturability thereof is superior.

Figure 9:
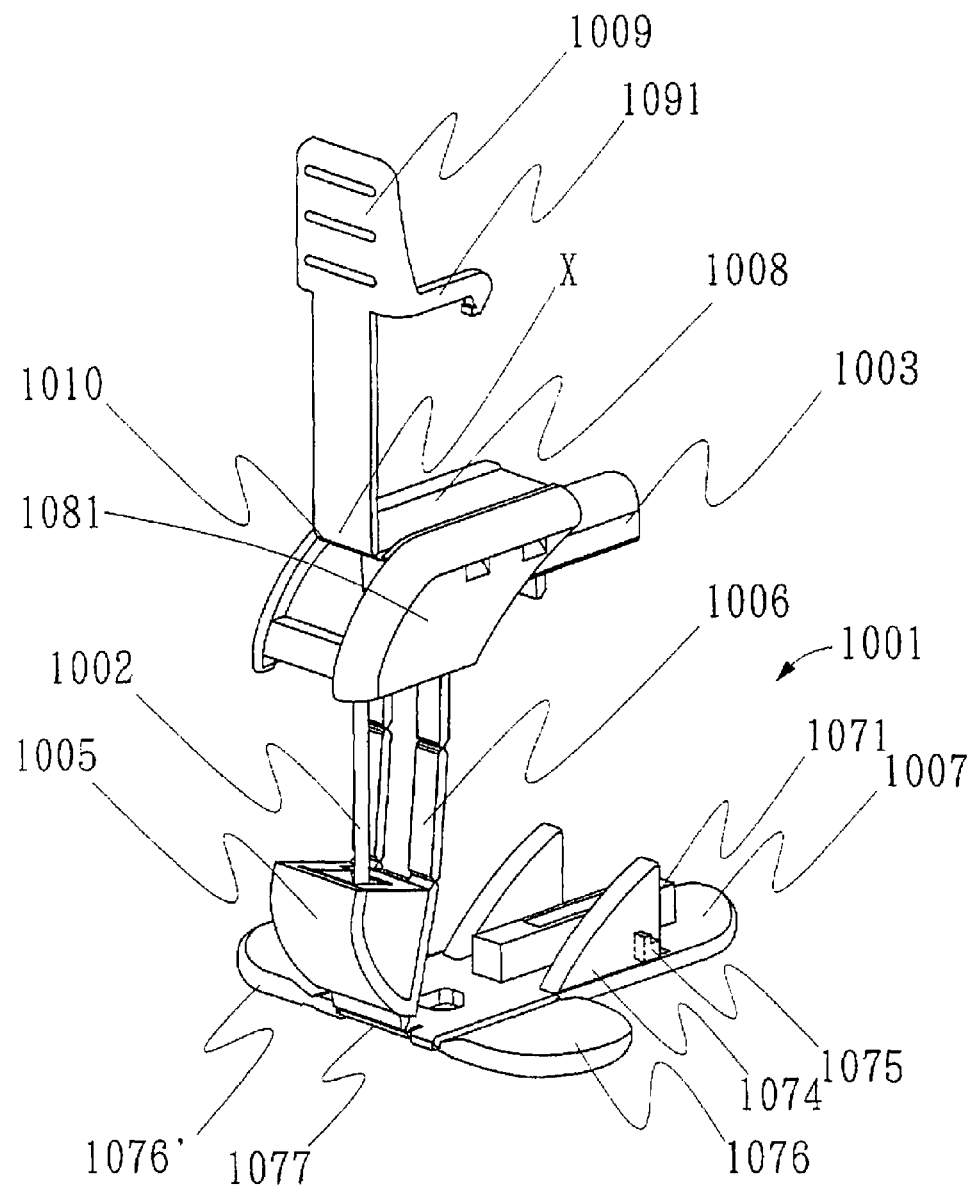
FIG. 9 is a perspective view of the post-use state of a third embodiment of the needle assembly of the present invention.
Figure 10:
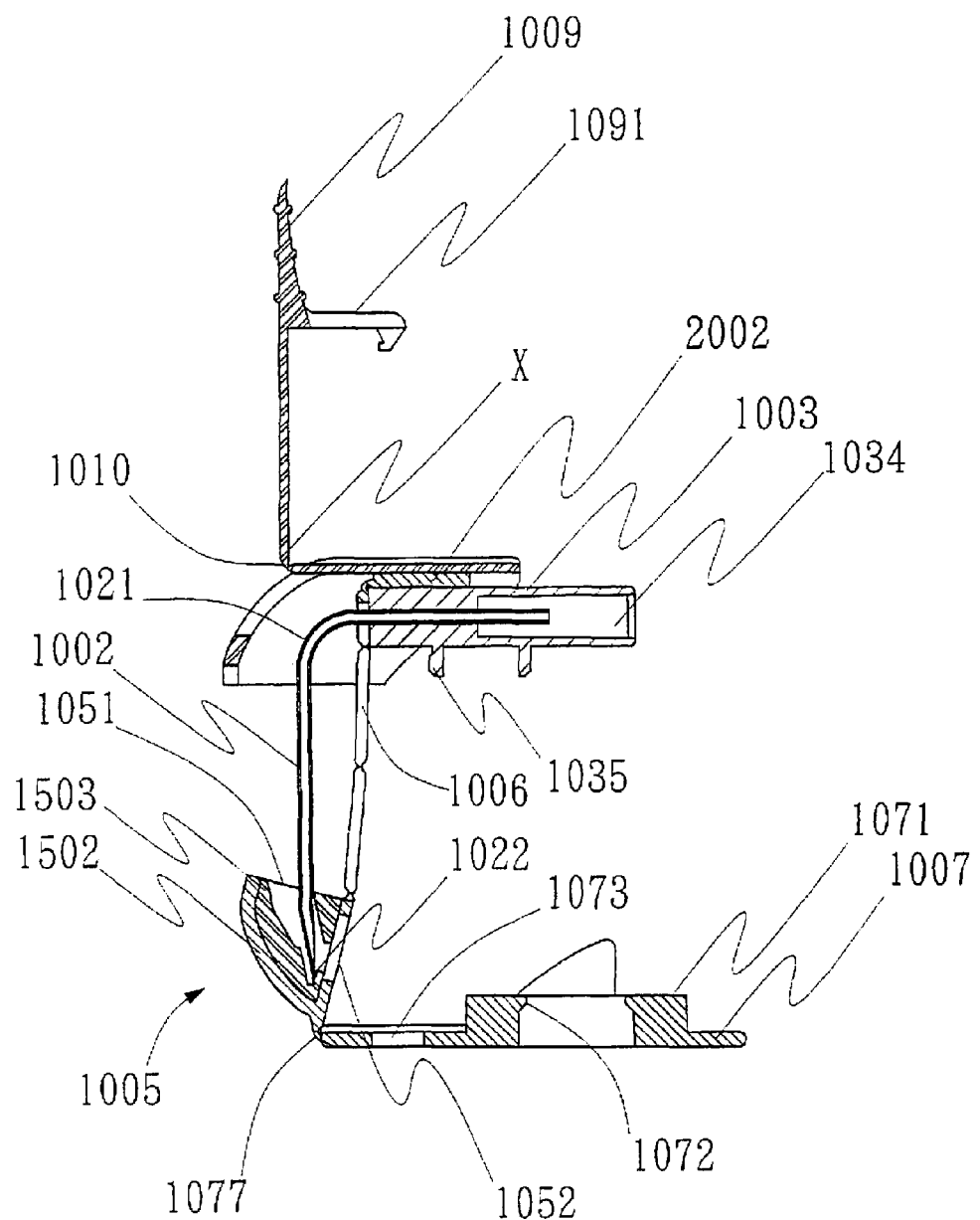
FIG. 10 is a cross-sectional view of the post-use state of a third embodiment of the needle assembly of the present invention.

FIG. 9 is a perspective view of a third embodiment of a needle assembly of the present invention showing the post-use state of a needle assembly 1001 when the distal tip end is housed. FIG. 10 is a vertical cross-sectional view of the needle assembly of the present invention in the state of FIG. 9. As shown in FIG. 10, the needle assembly 1001 includes a needle 1002 having a bend portion 1021 of approximately 90° bend, and a hub 1003 for holding a proximal end portion of the needle 1002. The needle assembly 1001 includes a distal end guarding portion 1005 for guarding the distal end of the needle 1002, a restraining portion 1006 constituted as a leg portion provided between the distal end guarding portion 1005 and the hub 1003, and a fixing portion 1007 that fixes to the skin and the like of a living body. In the needle assembly 1001, a cover member 1008 is provided in such a way as to cover the hub 1003 in which the needle 1002 is provided. A handle portion 1009 is provided in the upper portion of the cover member 1008 by way of a joining portion 1010 which functions as a joint. While in FIG. 9 the handle portion 1009 is provided in the needle assembly in such a way as to link with the hub 1003 of the needle 1002 having a bend portion 1021 of approximately 90° bend, a handle portion can be provided in a hub for a common needle in which there is no bend portion. The provision of the aforementioned handle portion in the hub allows the hub to be lifted up by the handle portion when the aforementioned needle assembly is converted from the insertion state to the withdrawn state. The needle can be easily withdrawn from the living body or the like as a result of the hub being lifted upward.

The aforementioned fixing portion 1007 is linked with the distal end guarding portion 1005 by way of a hinge portion 1077. The aforementioned needle 1002 is mounted in the hub 1003 in such a way as to lie substantially horizontally to the plane in which the living body is deployed, and the needle tip bends downward. While a Huber needle of a shape in which the cutting face is perpendicular to the direction of insertion of the needle is employed as the needle 1002 of the embodiment of FIG. 10, other surgical needles may also be employed. While the aforementioned bend of the bend portion in FIG. 10 is approximately 90°, there are no particular restrictions to the bend being approximately 90°. However, since the needle is able to be inserted into the living body by an operation involving merely a grip portion 1081 at both side faces of the hub 1003 being held between the fingers and pressed from above and, moreover, the needle tube is provided to extend in a direction horizontal to the deployment plane and, as a result, the arrangement of the needle tube is also simple, the bend of the bend portion is preferably approximately 90°.

In the embodiment of FIG. 9, a needle distal end portion 1022 of the needle 1002 is housed in the post-use state in the interior of the distal end guarding portion 1005 as shown in FIG. 10. Similarly to the embodiment of FIG. 1, the restraining portion 1006 prevents movement of the distal end guarding portion 5 toward the distal end from the state in which the needle tip is housed. In addition, the distal end guarding portion 1005 has a needle tip surrounding structure as shown in FIG. 10 constituted from an interior member 1503 and an exterior member 1502. Since the distal end guarding portion 5 encloses the needle distal end portion 1022 and because the positional relationship between the distal end guarding portion 1005 and the needle distal end portion 1022 is restricted by the restraining portion 1006, projection of the needle distal end portion 1022 beyond the needle tip surrounding structure to the exterior of the distal end guarding portion 1005 can be prevented. Furthermore, similarly to the embodiment of FIG. 1, the needle distal end portion 1022 of the needle 1002 is housed in the interior of the distal end guarding portion 1005 due to the flexibility of the needle and/or the needle-contacting section of the distal end guarding portion. Moreover, a tube (not shown in the figure) is connected to be inserted with a tube-connecting hole 1034 of the hub 1003 to afford communication between the cavity of the needle 1002 and the tube cavity.

Figure 11:
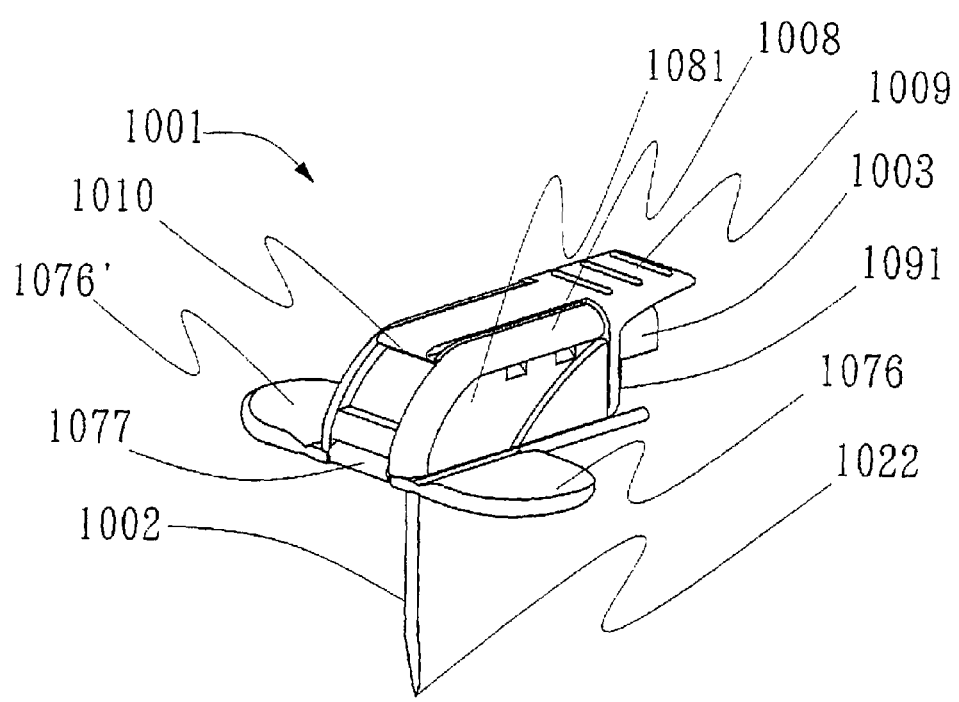
FIG. 11 is a perspective view of the pre-use state of the needle assembly of FIG. 9.
Figure 12:
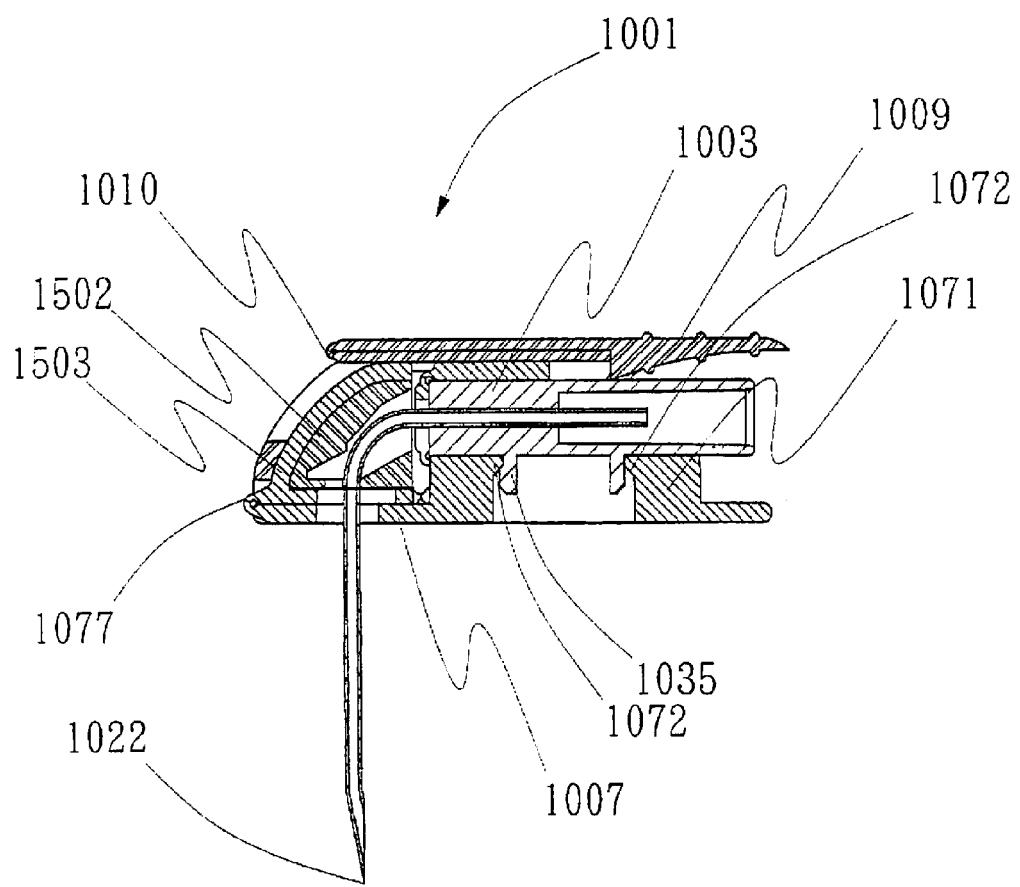
FIG. 12 is a cross-sectional view of the pre-use state of the needle assembly of FIG. 9.

FIG. 11 is a perspective view of the embodiment of FIG. 9 showing a pre-use state of the needle assembly 1001 of the present invention, and FIG. 12 is a vertical cross-sectional view of the needle assembly 1001 of the present invention of the state of FIG. 11. In the pre-use state of the needle assembly 1001 in which, as shown in FIG. 11, the restraining portion 1006 is provided in a folded state, a state in which the hub 1003 and the fixing portion 1007 are connected by an engaging portion 1032 of the hub 1003 and a connecting portion 1071 of the fixing portion 1007 is established. As shown in FIG. 9, the fixing portion 1007 includes a latching portion 1072 that latches to a connecting portion 1071, and the hub 1003 and the fixing portion 1007 are connected by the engagement of an engaging protrusion 1035 of the engaging portion 1032 with the latching portion 1072.

In addition, the needle 1002 in FIG. 11 is shown in a state in which it passes through a first aperture portion 1051 of the distal end guarding portion 1005 along the distal end guarding portion 1005 and, passing out of a second aperture portion 1052, it further passes through a needle passage 1073 of the fixing portion 1007 to project from the fixing portion 1007. In this pre-use state and when, for example, a medical solution is to be injected employing the needle assembly 1001, the grip portion 1081 in both sides of the cover member 1008 of the needle assembly 1001 is held between the fingers to insert the needle 1002 into the living body whereupon, by way of a tube (not shown in the figure) connected to the tube connecting hole 1034 and the cavity of the needle 1002, the medical solution can be injected into the living body or the like. Furthermore, conversion from the pre-use state of the needle assembly 1001 of FIG. 11 and FIG. 12 to the post-use state of FIG. 9 and FIG. 10 when the needle distal end is guarded can be implemented as follows. For the needle assembly 1001 in the state of FIG. 11 in which the needle 1002 is inserted into a living body or a port, by pressing wing portions 1076 and 1076' of the fixing portion 1007 deployed on the surface of the living body downward using the fingers of one hand while holding the grip portion 1081 in the fingers of the other hand and lifting up, the engagement between the fixing portion 1007 and the hub 1003 is released to afford the separation thereof and the establishment of the post-use state of FIG. 9 and FIG. 10 (state in which the needle tip is guarded). Furthermore, a protrusion to facilitate fixing using the fingers or for use as a slip guard may be provided in the grip portion 1081. In addition, as a different method of insertion, a method based on the wing portions being bent and the insertion being performed while holding a grip portion by way of these wing portions is also possible.

In the usage state of FIG. 11 and FIG. 12 of the needle assembly 1001, a hook portion 1092 of a clasp 1091 provided in the handle portion 1009 is engaged to be inserted in a hole 1075 of a clasp-accepting portion 1074 provided in a fixing portion 1007. As a result of this engagement, a state in which the handle portion 1009 is mounted in the cover member as shown in FIG. 11 is established. In the post-use state when the inserted needle assembly 1001 is withdrawn from the living body or the like, the front-end portion of the handle portion 1009 is lifted up to release the engagement thereof and establish the lifted-up state as shown in FIG. 9. The base end of the handle portion 1009 is attached to the cover member 1008 by way of the coupling portion 1010 to link with the hub 1003. By pressing wing portions 1076 and 1076' downward by the fingers of one hand and lifting up the handle portion 1009 held with the other hand in the vertical direction as shown in FIG. 9 and FIG. 10, the hub 1003 and needle 1002 are lifted up and the needle 1002 is withdrawn from the living body or the like into which it is inserted. When the needle 1002 is withdrawn, the base end X of the handle portion preferably lies approximately directly above the vertical portion of the needle 1002. The provision of the base end of the handle portion approximately directly above the vertical portion of the needle 1002 ensures that a pull-up force can be applied to the main body portion, which fixes the needle while covering the needle distal end portion with the base end of the handle portion serving as the origin, and ensures the needle 1002 can be lifted up without being caused to oscillate in either the distal end or proximal end directions. The provision thereof slightly above and to the distal end side in the horizontal direction from the vertical portion of the needle 1002 is more preferable from the standpoint of ease of housing the needle distal end portion in the distal end guarding portion. Furthermore, while in this embodiment the main body portion for supporting the needle is constituted from the needle hub and the cover member and the handle portion is coupled to the upper portion of the cover member, the handle portion may be directly provided in the main body portion or needle portion in such a way as to link with the needle hub.

Figure 13:
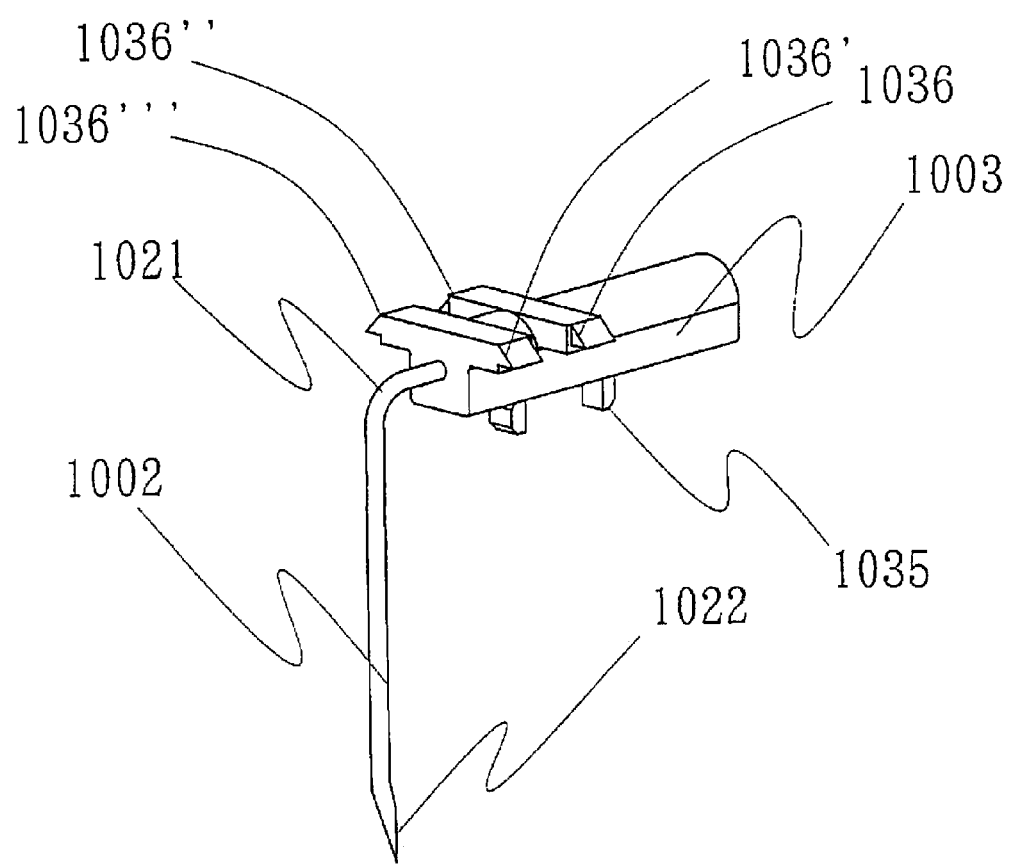
FIG. 13 is a perspective view of the needle and hub of the needle assembly of FIG. 9.
Figure 14:
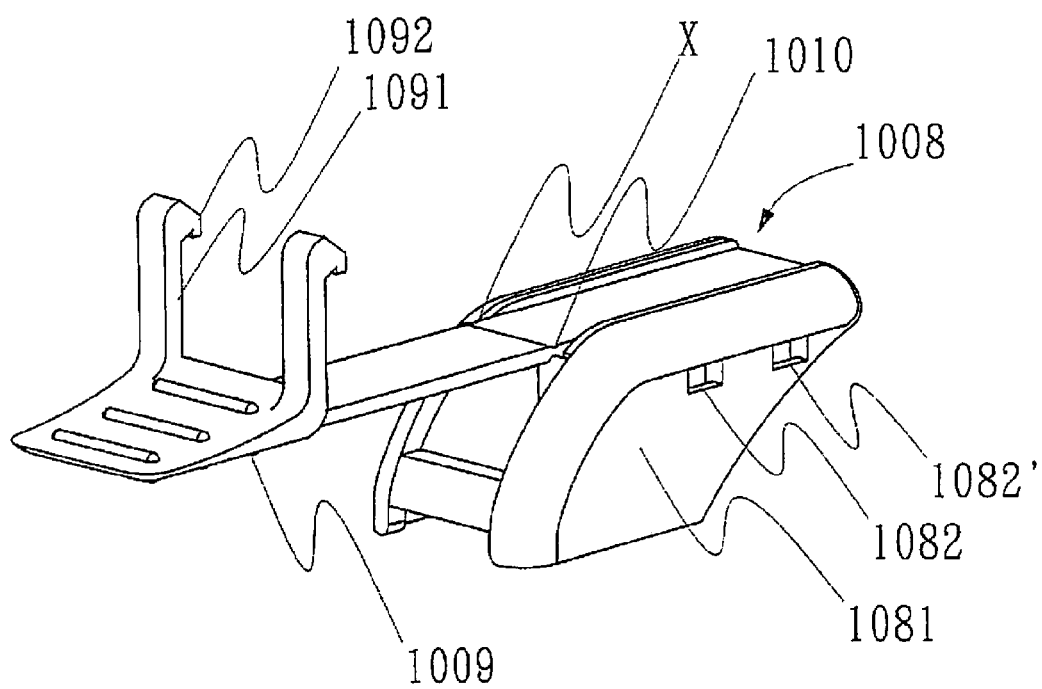
FIG. 14 is a perspective view of the cover member of the needle assembly of FIG. 9.

While there are no particular limitations to the configuration of the embodiment of FIG. 9, as an example thereof, the following configuration may be adopted. The needle hub includes a pair of engaging protrusions in its lower side as shown in FIG. 13, and pairs of convex portions 1036 and 1036' are respectively provided in both side faces thereof. Pairs of holes 1082 and 1082' are provided respectively in both side faces of the cover member attached in such a way as to cover the needle hub as shown in FIG. 14 and, when the cover member is attached to the needle hub, the aforementioned convex portions fit into the aforementioned holes. In addition, for the fixing portion, distal end guarding portion and restraining portion, a connection body 2001 in which the fixing portion, the distal end guarding portion and restraining portion are connected is formed as shown in FIG. 15, and a planar attachment portion 2002, in which a pair of protrusions 2021 is provided, is provided in the other end of the end portion of the restraining portion in which the distal end guarding portion is provided. The protrusions 2021 provided in the aforementioned attachment portion 2002 are provided at a width the same as the width between the convex portions 1036 and 1036' provided in one side face of the hub and, accordingly, in a state in which the aforementioned needle has passed along the first aperture portion and the second aperture portion of the distal end guarding portion, the aforementioned attachment portion is fitted to the upper side of the needle hub in such a way that the pair of aforementioned protrusions fit between the respective aforementioned convex portions. Furthermore, the attachment of the cover member to the needle hub from above the aforementioned attachment portion ensures ease of assembly of the third embodiment of the needle assembly of the present invention. Furthermore, in the embodiment of FIG. 9, while a connection body 2001 in which a fixing portion, distal end guarding portion and restraining portion are connectively and integrally provided is employed, the employment of a connection body in which these elements are integrated is not a requisite constituent element of the present invention for needle tip guarding. However, as shown in FIG. 15 for example, for a connection body in which hinge portions are respectively provided between each of the fixing portions, the distal end guarding portion, the restraining portion and the attachment portion in that sequence, arbitrary angles can be adopted between mutually adjacent sections thereof and, accordingly, the assembly of the needle assembly is simple and, moreover, this is further desirable in that transformation from the pre-use state to the post-use state thereof can be smoothly implemented, thereby simplifying the needle tip guarding. Furthermore, the coupling may be accomplished by adhesion instead of fitting.

Figure 16:
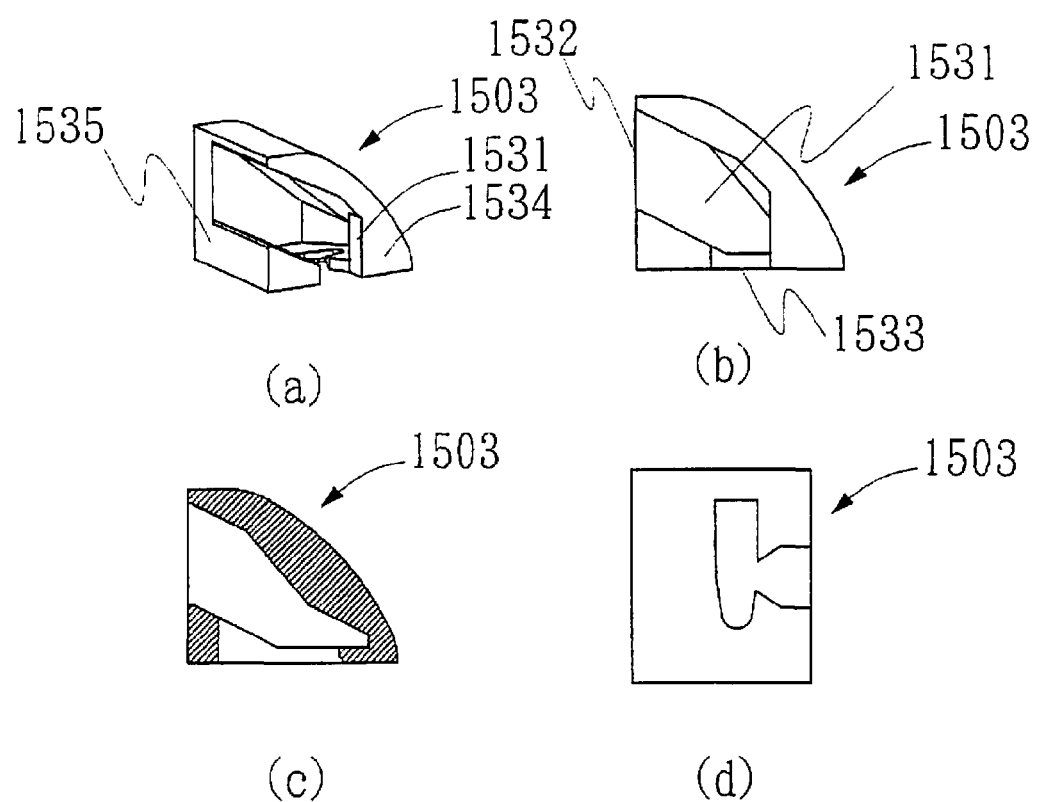
FIG. 16 A is a perspective view from the rear of the distal end guarding member of the needle assembly of FIG. 9, B is a right-side view of the distal end guarding member of A, C is a vertical cross-sectional view of the distal end guarding member of A, and D is a base view of the distal end guarding member of A.

The distal end guarding portion of the embodiment of FIG. 9 is constituted from two members and includes an exterior member 1502 and interior member 1503. The interior member 1503 includes a side-aperture portion 1531 in one side face. Similarly to the embodiment shown in FIG. 1, an interior member having a needle tip surrounding structure may be employed. The side-aperture portion 1531 includes a second aperture end 1533 at the boundary between a right-side face 1534 and base face, and a first aperture end 1532 at the boundary between the right-side face 1534 and rear face 1535. As shown in FIG. 16, the shape of the side-aperture portion 1531 corresponds to the bend portion of the needle 1002, which defines a shape in which the section of the needle 1002 extending in the vertical direction passes through the second aperture end 1533 and the section of the needle 1002 extending in the horizontal direction passes through the first aperture end 1532 so that the bend portion, passing through the side-aperture portion, is housed in the interior of the interior member. By the adoption of a distal end guarding portion of an interior member of a shape such as this as the aforementioned distal end guarding portion, a pre-use state as shown in FIG. 11 of a connection body, needle and needle hub is established by attachment of an attachment portion to the upper portion of the aforementioned needle hub and the engaging protrusions of the needle hub being caused to engage with the engagement-receiving portions and, as a result of the aforementioned interior member being fitted through the side face of the aforementioned exterior member and being covered from above by a cover member, damage to the needle tip can be prevented and, moreover, the needle assembly can be easily assembled.

The restraining portion of the embodiment of FIG. 9 is identical to the restraining portion of the embodiment of FIG. 1 and, provided the restraining portion is satisfactorily able to demonstrate a function of restricting the distance between the distal end guarding portion and the hub and is able to inhibit re-protrusion of the needle tip from the distal end guarding portion to the exterior, there are no particular limitations thereto. Furthermore, while the restraining portion able to demonstrate this function of the present invention described above is shown as a pair of leg portions, the restraining portion may describe a ladder-like shape or a plate shape.

The invention claimed is:

1. A needle assembly comprising a needle having a cutting blade formed in a distal end, a hub for holding a proximal end portion of the needle, and a distal end guarding portion, the needle assembly comprising:

a restraining portion for restricting a distance between the distal end guarding portion and the hub; and, a fixing portion connected to the distal end guarding portion via a hinge portion, wherein the distal end guarding portion rotates via the hinge portion, with respect to the fixing portion, and the distal end guarding portion has a first aperture portion arranged at a proximal end of the needle, a second aperture portion arranged at a distal end of the needle, and a needle tip retraction preventing portion arranged at the second aperture portion; and, an opening of the first aperture portion and an opening of the second aperture portion form an angle with respect to each other, wherein the needle, in a pre-usage stage, is inserted into a distal end guarding portion from the first aperture portion of the distal end guarding portion and is in a state withdrawn from the second aperture portion, and after usage, moves from the second aperture portion by the needle, which is in contact with the needle tip retraction preventing portion, flexing, and the distal end of the needle is guarded by the needle tip being housed inside the distal end guarding portion in a state of being engaged with the distal end guarding portion.

2. The needle assembly according to claim 1, wherein the needle, which is in contact with the needle tip retraction preventing portion, flexes with the first aperture portion as a support point.

3. The needle assembly according to claim 1, wherein the needle has a bend portion, and a fixing portion is provided in the distal end guarding portion.

4. The needle assembly according to claim 1, wherein the fixing portion is provided in the distal end guarding portion, and the fixing portion has a needle passage through which the needle is able to move in an axial direction.

5. The needle assembly according to claim 1, wherein the restraining portion forms a folded structure in the pre-use state.

6. The needle assembly according to claim 1, wherein the needle is a Huber needle.

7. The needle assembly according to claim 1, wherein a bend of the bend portion is a substantially 90° bend.

8. The needle assembly according to claim 1, wherein the needle assembly further comprises a handle portion that links with the needle hub, the handle portion being provided in the needle assembly in such a way that, as a result of being pulled upward during conversion from an insertion state of the needle assembly to a withdrawn state of the needle, the hub is lifted up by way of a coupling portion.

9. The needle assembly according to claim 8, wherein the handle portion has a clasp by which the handle portion engages with the fixing portion, the handle portion being provided to be turnable so that a front-end portion thereof describes an arc a center thereof is the coupling portion, and the engagement between the handle portion and the fixing portion being released by lifting up an end portion of the handle portion.

10. The needle assembly according to claim 8, wherein the handle portion is linked with the needle hub by way of the coupling portion, the coupling portion being provided in a horizontal direction of the needle in a position substantially directly above a vertical portion from which the distal end-side from the bend portion of the needle is constituted.

11. The needle assembly according to claim 10, the needle assembly comprising a cover member that in the insertion state covers the distal end guarding portion and connects with the hub, wherein the handle portion is provided in the cover member by way of the coupling portion.

12. The needle assembly according to claim 11, the needle assembly including a connection body comprising the fixing portion, the distal end guarding portion and the restraining portion, wherein the connection body further comprises an attachment portion, the attachment portion being fixed to the hub between the hub and the cover member.

13. A needle mechanism comprising a needle in which a cutting blade is formed in a distal end; a hub for holding a proximal end portion of the needle; and a distal end guarding portion which protects a needle tip, wherein the needle mechanism comprises: a restraining portion for restricting a distance between the distal end guarding portion and the hub, and a fixing portion connected to the distal end guarding portion via a hinge portion, wherein the distal end guarding portion rotates via the hinge portion with respect to the fixing portion connected by the hinge portion, and the distal end guarding portion has a first aperture portion arranged at a proximal end of the needle, a second aperture portion arranged at a distal end of the needle, and a needle tip retraction preventing portion arranged at the second aperture portion; and an opening of the first aperture portion and an opening of the second aperture portion form an angle with respect to each other, wherein the needle, in a pre-usage stage, is inserted into a distal end guarding portion from the first aperture portion of the distal end guarding portion and is in a state withdrawn from the second aperture portion, and after usage, moves from the second aperture portion by the needle, which is in contact with the needle tip retraction preventing portion, flexing, and the distal end of the needle is guarded by the needle tip being housed inside the distal end guarding portion in a state of being engaged with the distal end guarding portion.

14. The needle mechanism according to claim 13, wherein the needle, which is in contact with the needle tip retraction preventing portion, flexes with the first aperture portion as a support point.

* * * * *